United States Patent
Lieberman et al.

(10) Patent No.: US 8,012,127 B2
(45) Date of Patent: Sep. 6, 2011

(54) SYSTEMS AND METHODS FOR GAINING ACCESS AROUND AN IMPLANTED MEDICAL DEVICE

(75) Inventors: Randy A. Lieberman, Bloomfield, MI (US); Steven L. Waldhauser, Circle Pines, MN (US); Javier J. Echenique, Miami, FL (US); Lonnie D. Ronning, Coon Rapids, MN (US); Linnea R. Lentz, Stacy, MN (US); Kimberly A. Oleson, Shoreview, MN (US); Deanna K. Levenhagen, Blaine, MN (US); Phillip C. Falkner, Minneapolis, MN (US); Michael W. Kimmel, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 377 days.

(21) Appl. No.: 11/680,346

(22) Filed: Feb. 28, 2007

(65) Prior Publication Data

US 2008/0208133 A1 Aug. 28, 2008

(51) Int. Cl.
*A61M 5/178* (2006.01)

(52) U.S. Cl. ............ 604/160; 604/161; 604/164.05

(58) Field of Classification Search ......... 604/160–161, 604/164.05, 166.01, 528–529, 523–527, 604/503, 508–510, 192, 194, 264; 606/194, 606/171

See application file for complete search history.

(56) References Cited

U.S. PATENT DOCUMENTS

| | | | | |
|---|---|---|---|---|
| 3,550,591 | A * | 12/1970 | MacGregor | 604/161 |
| 4,054,136 | A * | 10/1977 | von Zeppelin | 604/160 |
| 4,921,479 | A * | 5/1990 | Grayzel | 604/509 |
| 4,988,356 | A * | 1/1991 | Crittenden et al. | 606/192 |
| 5,003,990 | A | 4/1991 | Osypka | |
| 5,015,239 | A | 5/1991 | Browne | |
| 5,246,014 | A | 9/1993 | Williams et al. | |
| 5,312,360 | A * | 5/1994 | Behl | 604/164.1 |
| 5,318,588 | A * | 6/1994 | Horzewski et al. | 606/198 |
| 5,334,187 | A * | 8/1994 | Fischell et al. | 604/102.02 |
| 5,447,503 | A | 9/1995 | Miller | |
| 5,693,030 | A * | 12/1997 | Lee et al. | 604/117 |
| 5,713,867 | A * | 2/1998 | Morris | 604/164.05 |
| 5,957,968 | A | 9/1999 | Belden et al. | |

(Continued)

FOREIGN PATENT DOCUMENTS

WO 0134238 5/2001

OTHER PUBLICATIONS

PCT Search Report for PCT/US2008/055336, Mailed Oct. 11, 2008.

*Primary Examiner* — Theodore Stigell
*Assistant Examiner* — Larry R Wilson

(57) ABSTRACT

Systems for gaining access into a body of a patient around an implanted body of an elongate medical device include a sheath having a deformable wall that allows insertion of the device body into a lumen surrounded by the sheath wall. The sheath wall may include first and second edges that extend from a proximal end to a distal end of the lumen, or just extend along a distal portion of the lumen. A tool, which includes a groove sized to grasp about a circumference of the device body, may facilitate insertion of the device body into the lumen of those sheath embodiments that include the first and second edges, by spreading at least one of the first and second edges of the wall apart from the other of the first and second edges while the device body is grasped within the tool.

4 Claims, 18 Drawing Sheets

U.S. PATENT DOCUMENTS

| | | | |
|---|---|---|---|
| 6,110,164 A * | 8/2000 | Vidlund | 604/524 |
| 6,159,198 A * | 12/2000 | Gardeski et al. | 604/523 |
| 6,185,464 B1 | 2/2001 | Bonner et al. | |
| 6,497,681 B1 | 12/2002 | Brenner | |
| 6,522,932 B1 | 2/2003 | Kuzma et al. | |
| 7,092,765 B2 | 8/2006 | Geske et al. | |
| 2004/0064147 A1 * | 4/2004 | Struble | 606/129 |
| 2005/0256503 A1 * | 11/2005 | Hall | 604/523 |
| 2007/0079511 A1 * | 4/2007 | Osypka | 30/90.1 |
| 2007/0175049 A1 | 8/2007 | Goode | |

\* cited by examiner

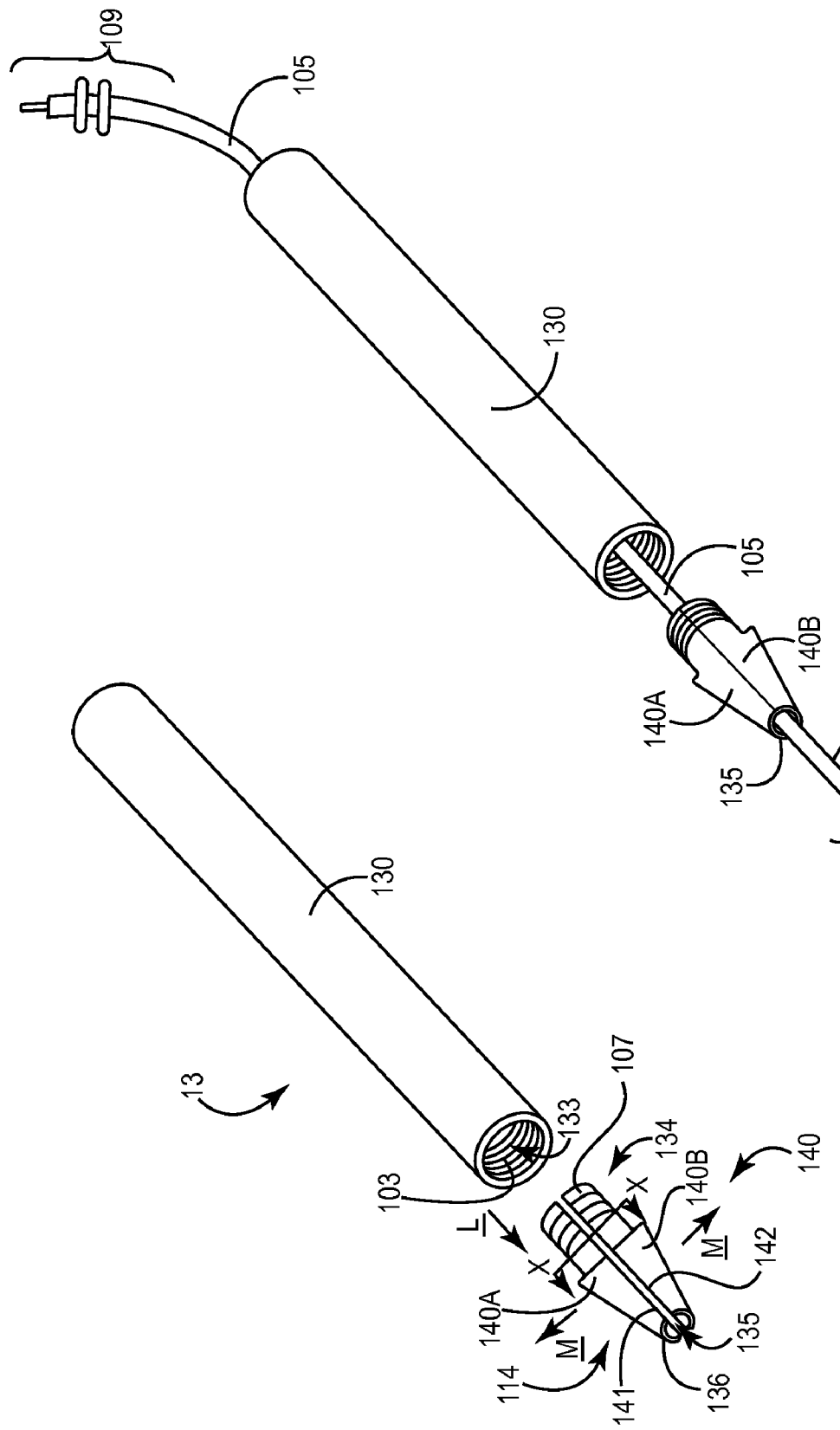

SYSTEMS AND METHODS FOR GAINING ACCESS AROUND AN IMPLANTED MEDICAL DEVICE

TECHNICAL FIELD

The present invention is related to systems and methods for implanting elongate medical devices, and more particularly to systems and methods for gaining venous access to facilitate the implantation procedure.

BACKGROUND

Many medical devices, for example, medical electrical leads and drug delivery catheters, include elongate bodies facilitating therapy delivery and/or diagnostic sensing; the bodies often include lumens extending along a longitudinal axis thereof. Such a lumen may provide a passageway for a stylet or guidewire that helps to guide the device to a target site within a body of a patient, for example, within a chamber of the heart. In recent years, the space used for guidewire/stylet lumens within elongate bodies of many medical devices has either been eliminated, to downsize the device bodies, or used for other purposes, for example, for the routing of one or more additional lead wires that add functionality to the device. Delivery catheters have been developed to guide these elongate medical devices, which do not have stylet/guidewire lumens, to a target implant site, and these devices are sometimes designated as "catheter-delivered" devices.

In order to implant the elongate body of a medical device in the venous system, for example, a right atrium, a right ventricle or a coronary sinus, an implanting physician first obtains venous access by inserting an introducer sheath into an access site, for example, in the cephalic, sub-clavian, or axillary vein, according to methods known to those skilled in the art. The implanter may then insert a catheter delivered medical device within a delivery catheter lumen, either before or after inserting the delivery catheter into the venous system through the introducer sheath. Once the delivery catheter has been steered or directed to a target implant site within the venous system, the implanter advances the medical device through the catheter lumen and out through a distal tip to fix a distal end of the device at the site. After the medical device is fixed, the implanter typically removes the introducer sheath and/or the catheter from the venous system, typically by splitting a wall of each to peel, or slit them away from around a proximal portion of the medical device body that extends out from the venous system. In some cases, after removing the introducer sheath and catheter, the implanter discovers that the distal end of the medical device has become dislodged, or that the distal end needs to be repositioned to provide better therapy delivery and/or diagnostic sensing. Since the catheter delivered device does not include a stylet or guidewire lumen, there is a need to re-gain venous access around the device, in order that another delivery catheter can be inserted into the venous system to reposition the device. Similar situations may arise for elongate devices implanted, via a delivery catheter, within other portions of a patient's body outside the venous system, for example, for epicardially implanted devices.

BRIEF DESCRIPTIONS OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

Figure 4B:
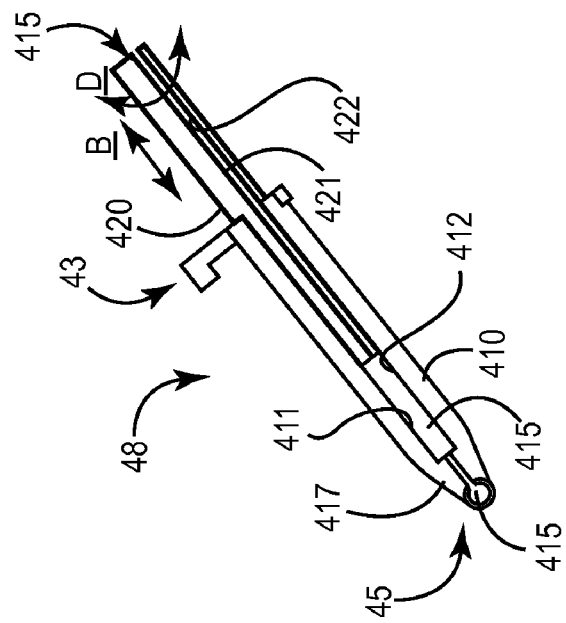
Figure 4A:
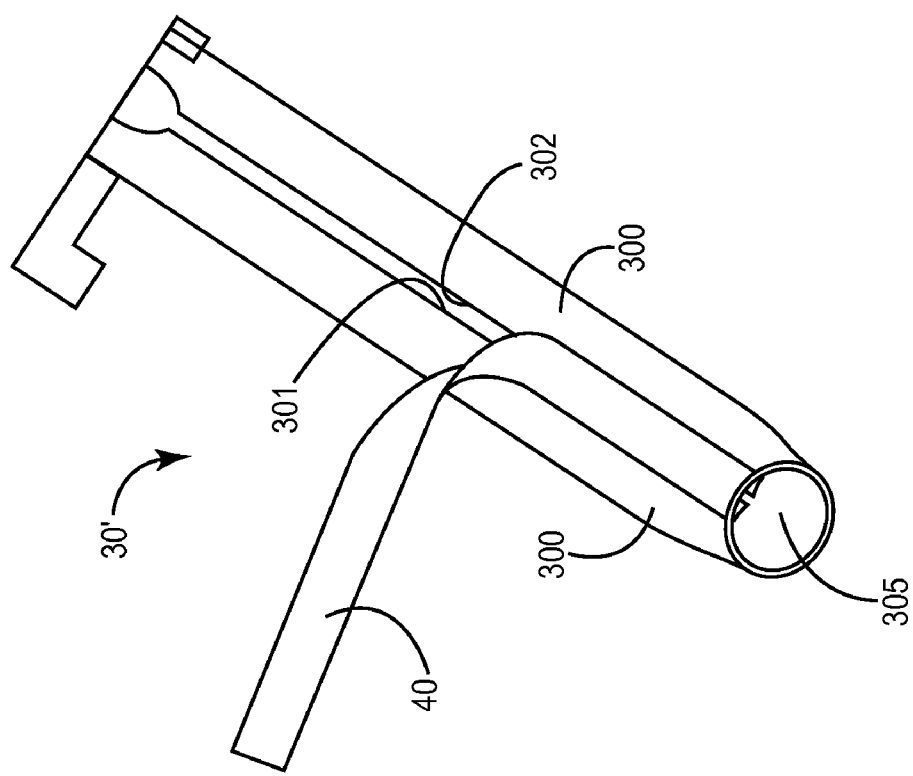

FIGS. 4A-B are perspective views of alternate embodiments of access sheaths.

Figure 5A:
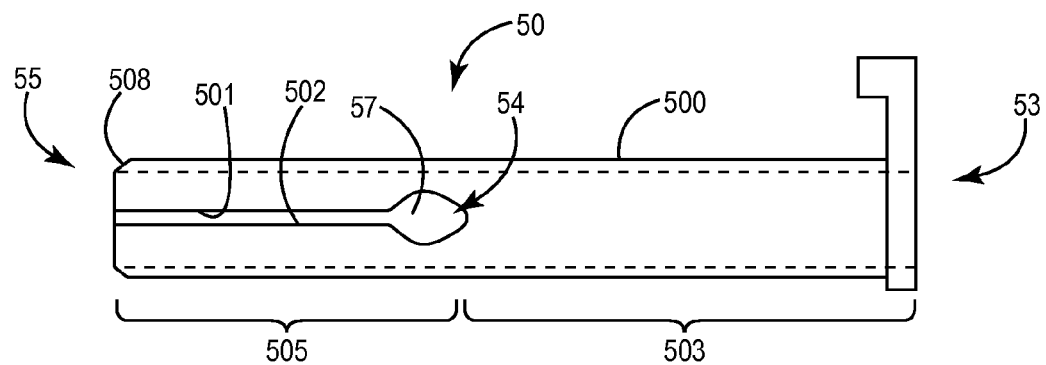

FIG. 5A is a plan view of an access sheath, according to another embodiment of the present invention.

Figure 5B:
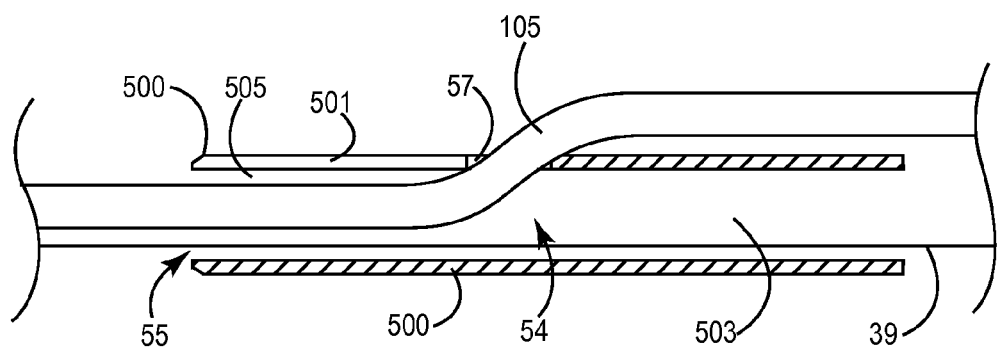

FIG. 5B is a longitudinal section view through the sheath of FIG. 5A in which the device body is inserted.

Figure 6A:
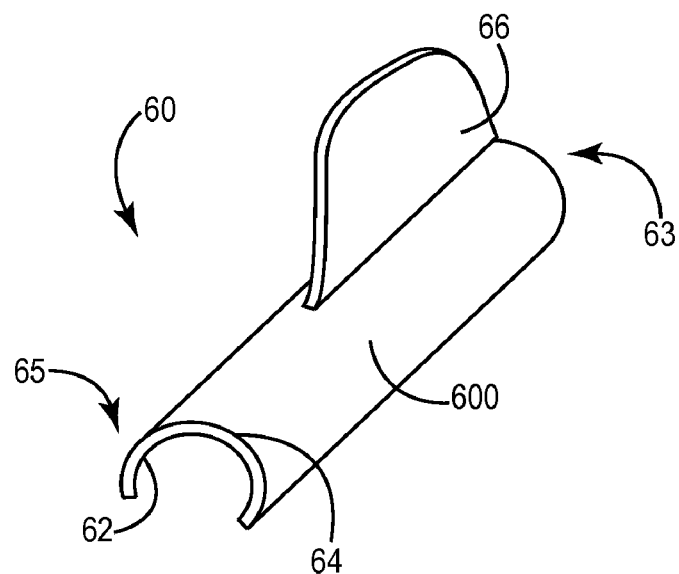

FIG. 6A is a perspective view of an insertion tool, according to some embodiments of the present invention.

Figure 3A:
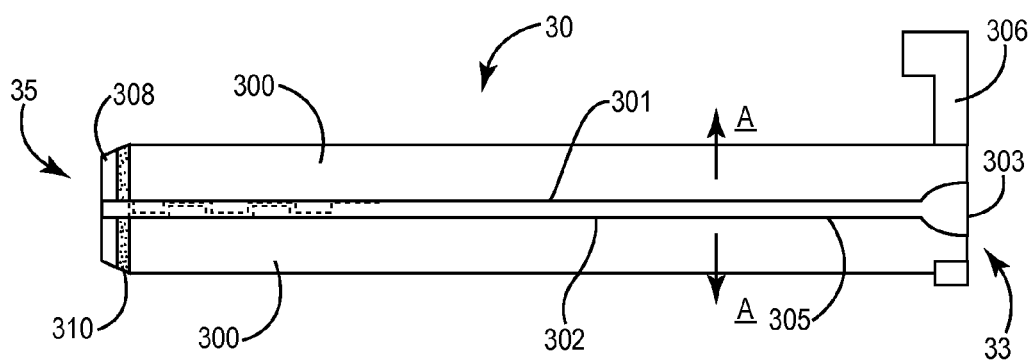
FIG. 3A is a plan view of an access sheath, according to some embodiments of the present invention.
Figure 3B:
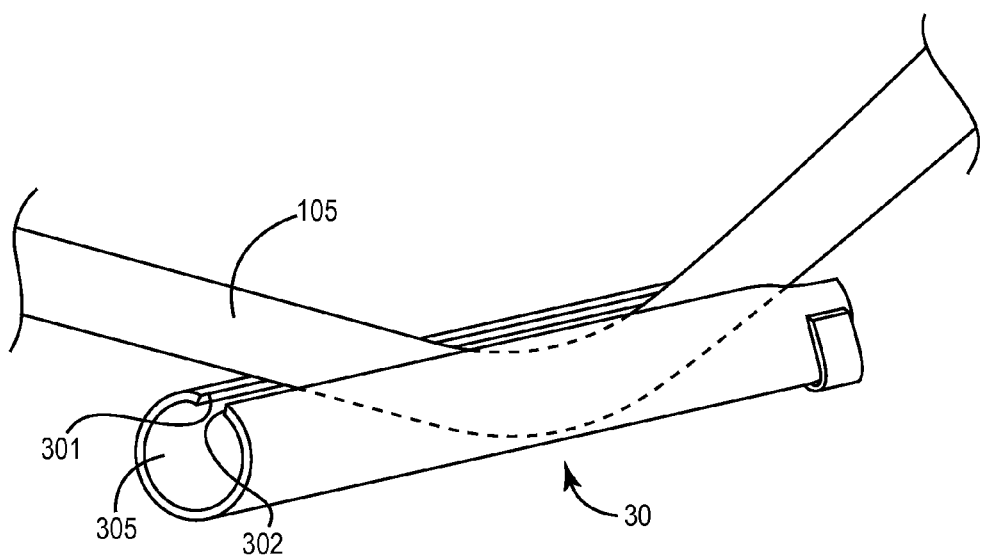
FIG. 3B is a perspective view of the device body being inserted into a lumen of the access sheath of FIG. 3A.
Figure 3C:
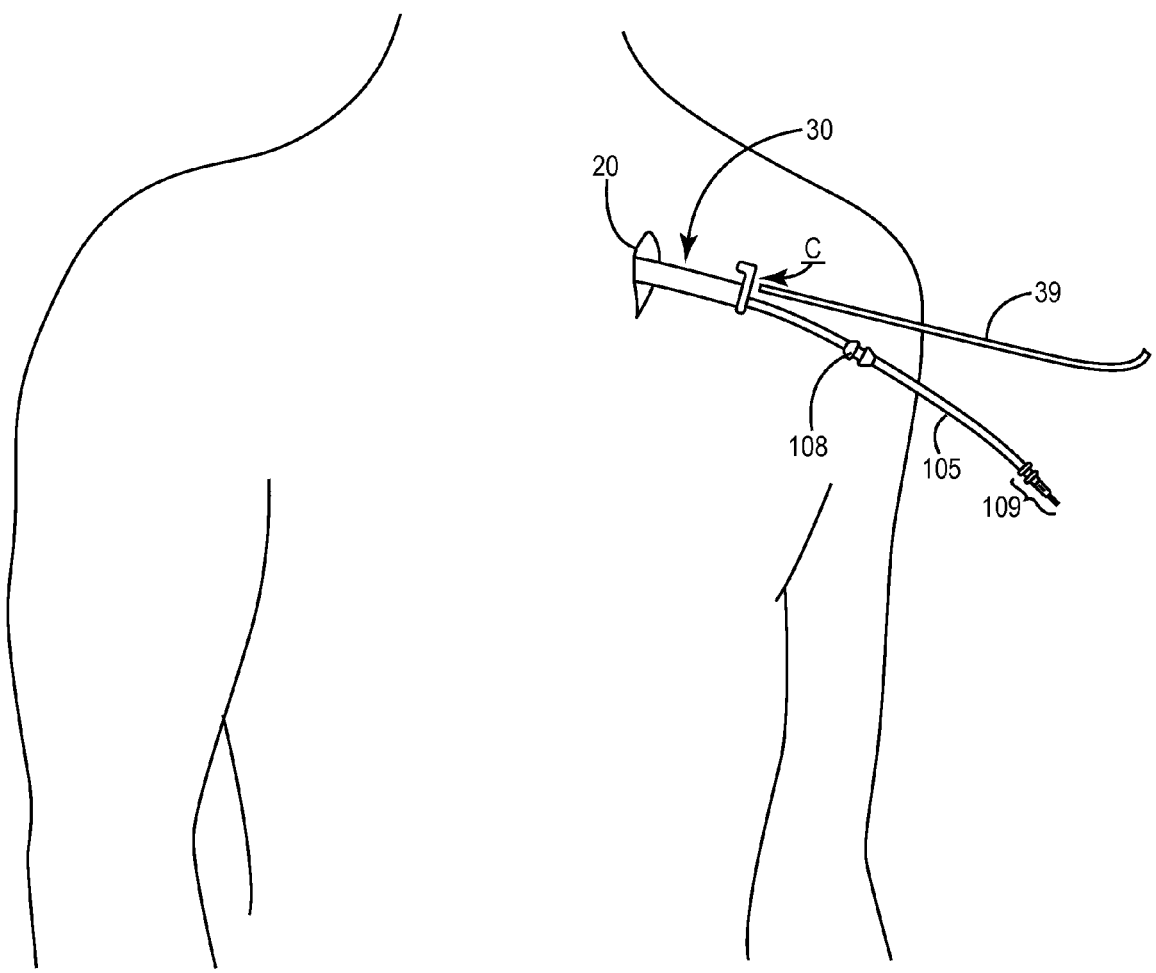
FIG. 3C is a schematic depiction showing the sheath inserted into the venous system, around the device body, at the access site.
Figure 6B:
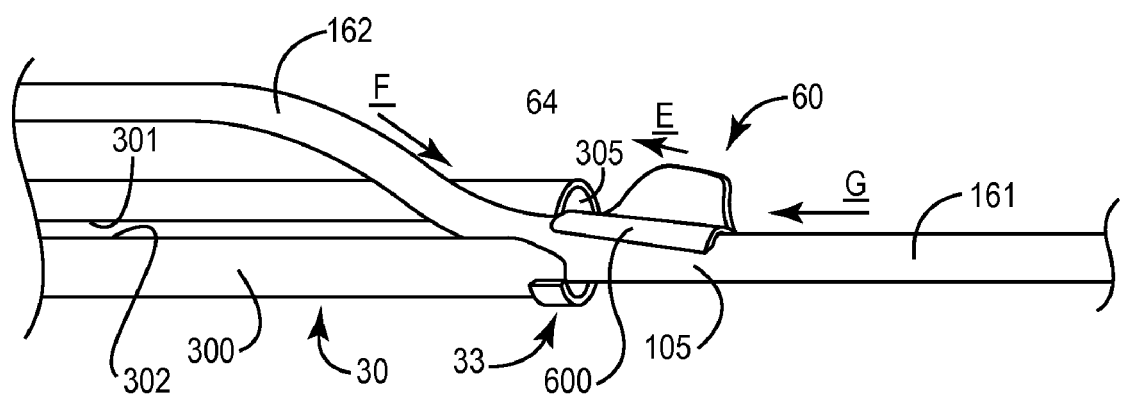

FIG. 6B is a perspective view of the tool of FIG. 6B mounted on the elongate device body to draw the body into a lumen of the access sheath of FIGS. 3A-C, according to some embodiments of the present invention.

Figure 7A:
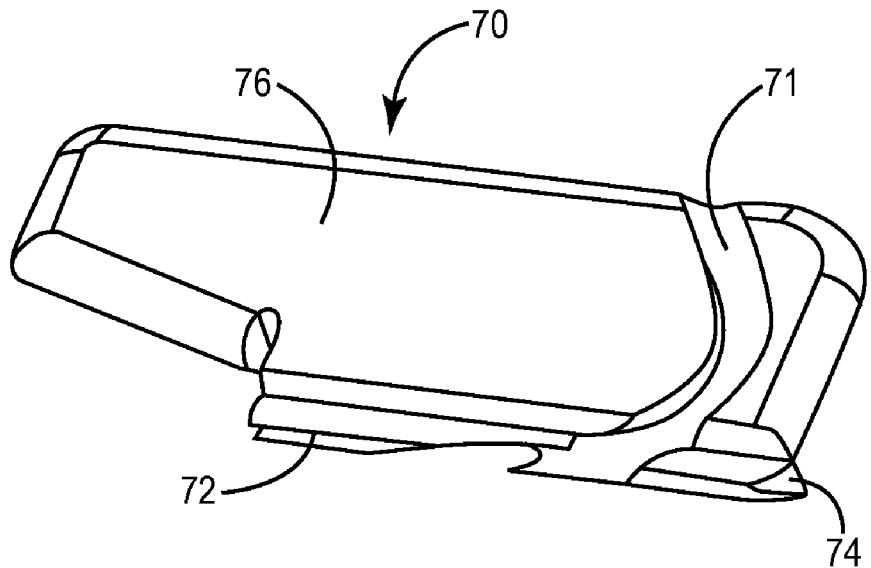

FIG. 7A is a perspective view of another insertion tool, according to alternate embodiments of the present invention.

Figure 7B:
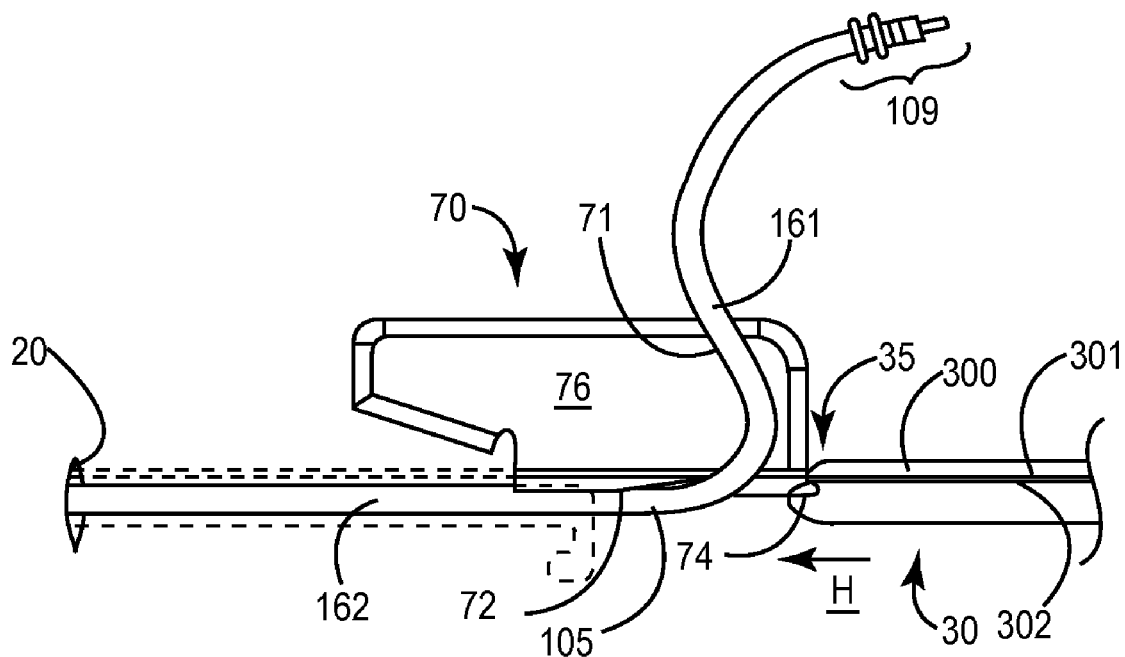

FIG. 7B is a plan view of the tool of FIG. 7A mounted on the elongate device body and engaged with the access sheath.

Figure 8A:
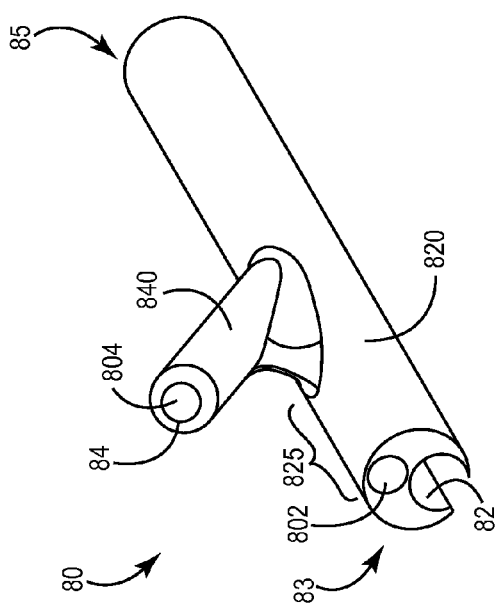

FIG. 8A is a perspective view of yet another insertion tool, according to additional embodiments of the present invention.

Figure 8B:
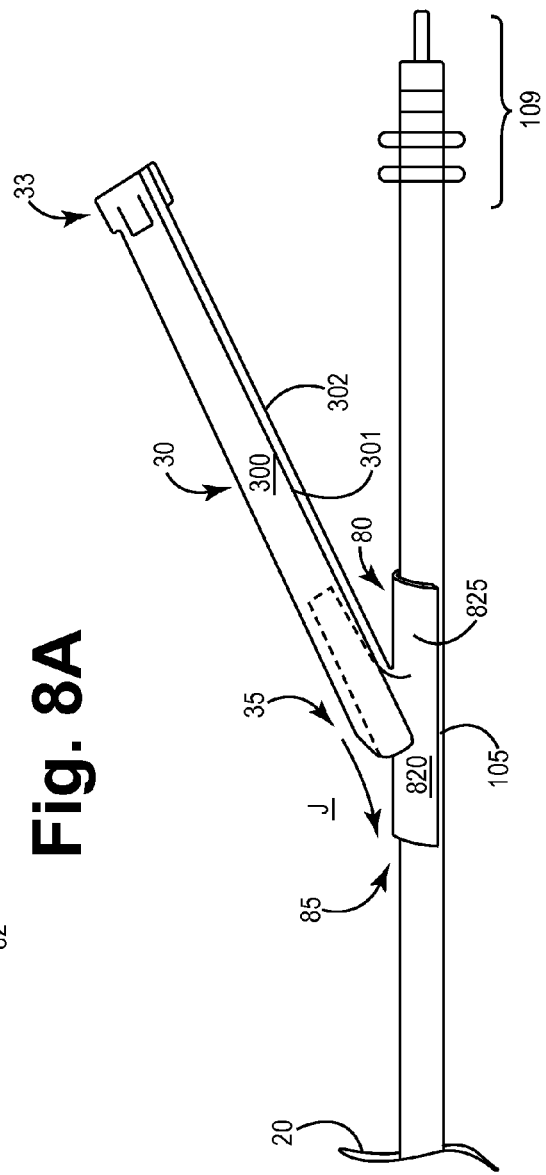

FIG. 8B is a plan view of the tool of FIG. 7A mounted on the elongate device body, and the access sheath mounted on the tool.

Figure 8C:
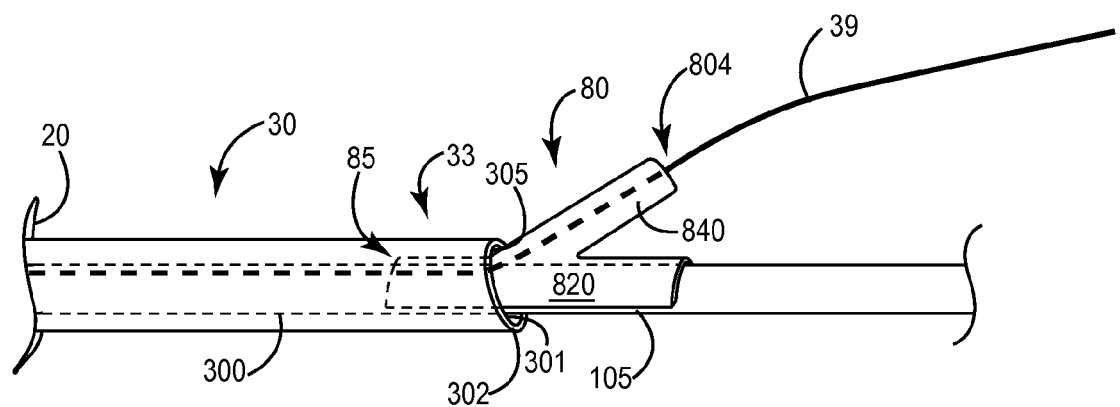

FIG. 8C is a plan view of the sheath having been passed over the tool of FIGS. 8A-B and the device body.

Figure 9A:
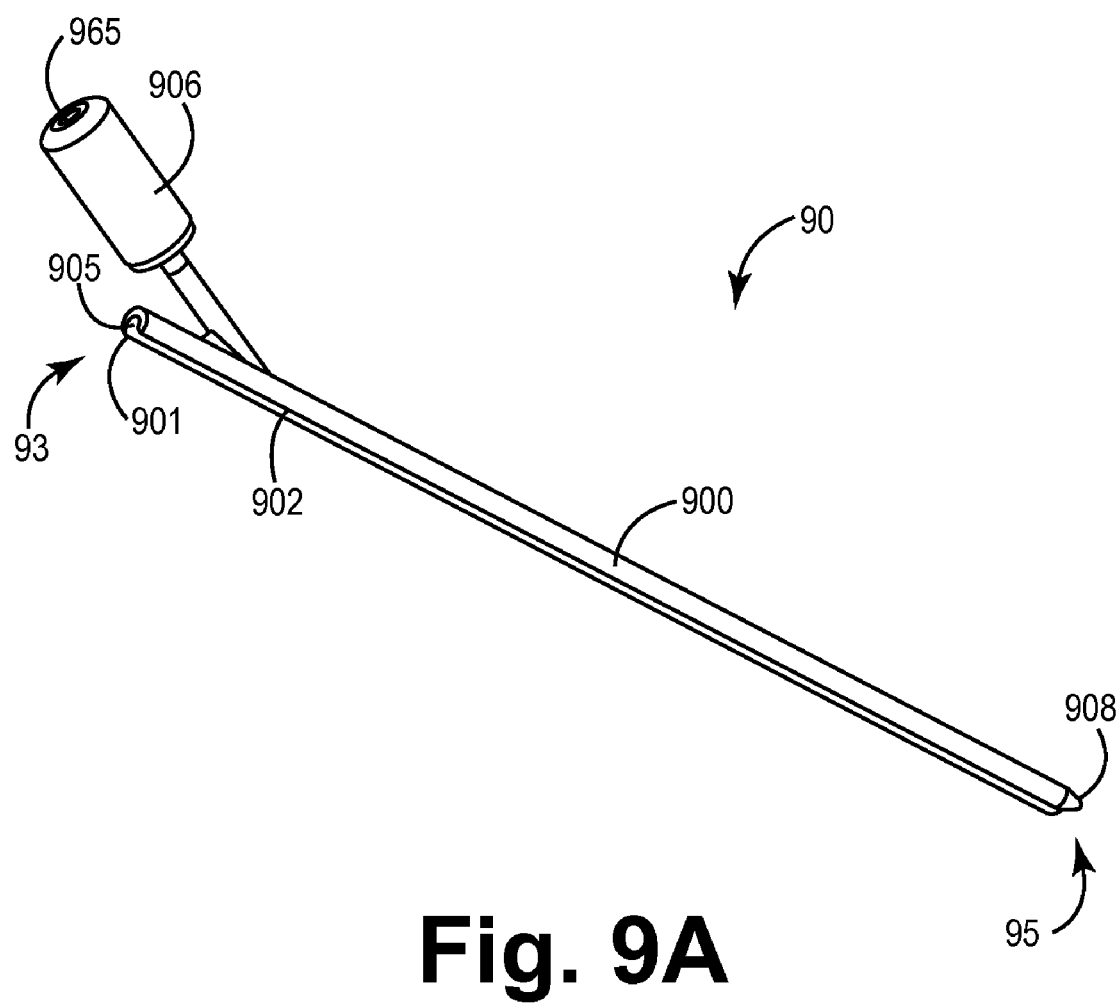

FIG. 9A is a perspective view of an access sheath, according to additional embodiments of the present invention.

Figure 9B:
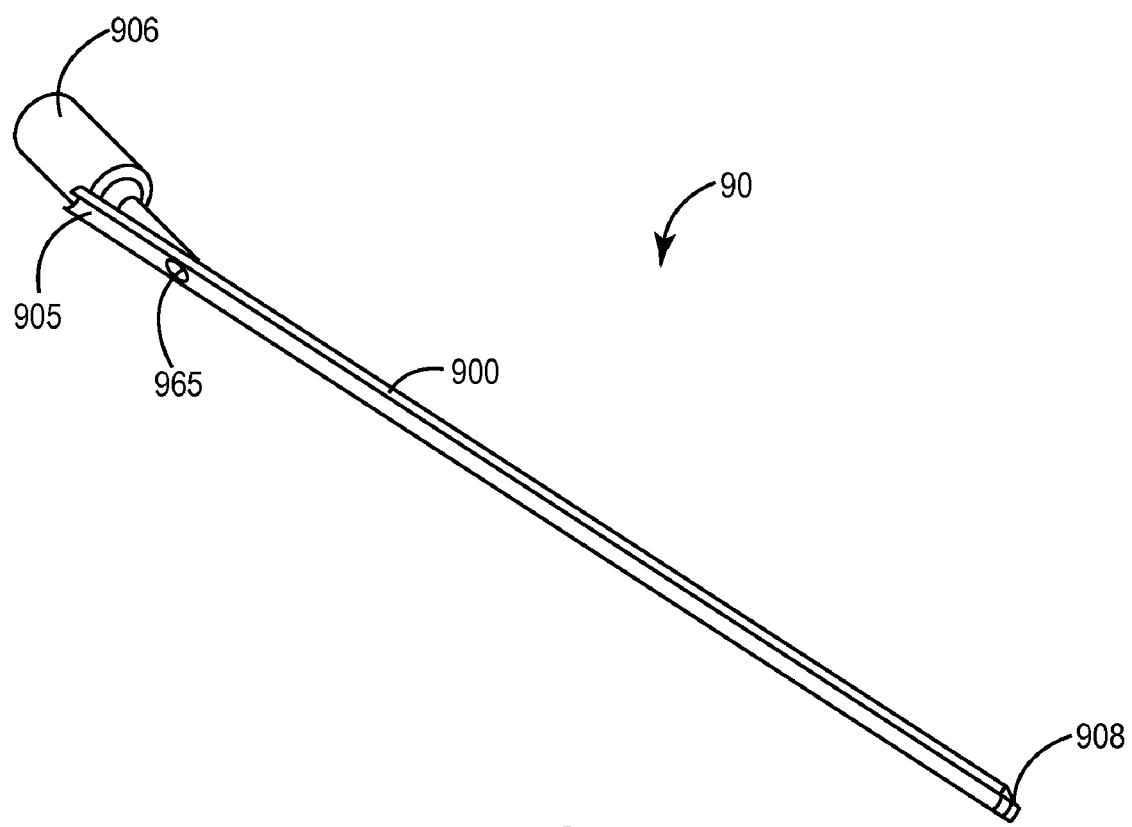

FIG. 9B is another perspective view of the access sheath of FIG. 9A, according to some embodiments.

Figure 9C:
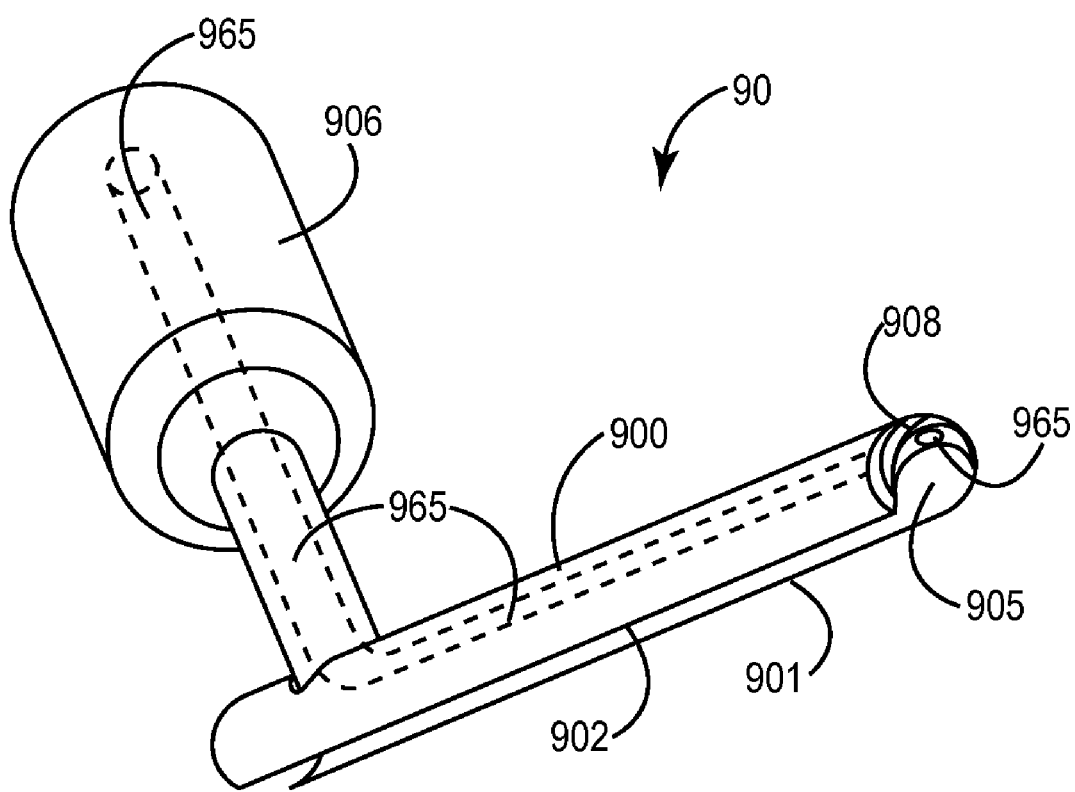

FIG. 9C is another perspective view of the access sheath of FIG. 9A, according to some other embodiments.

Figure 9D:
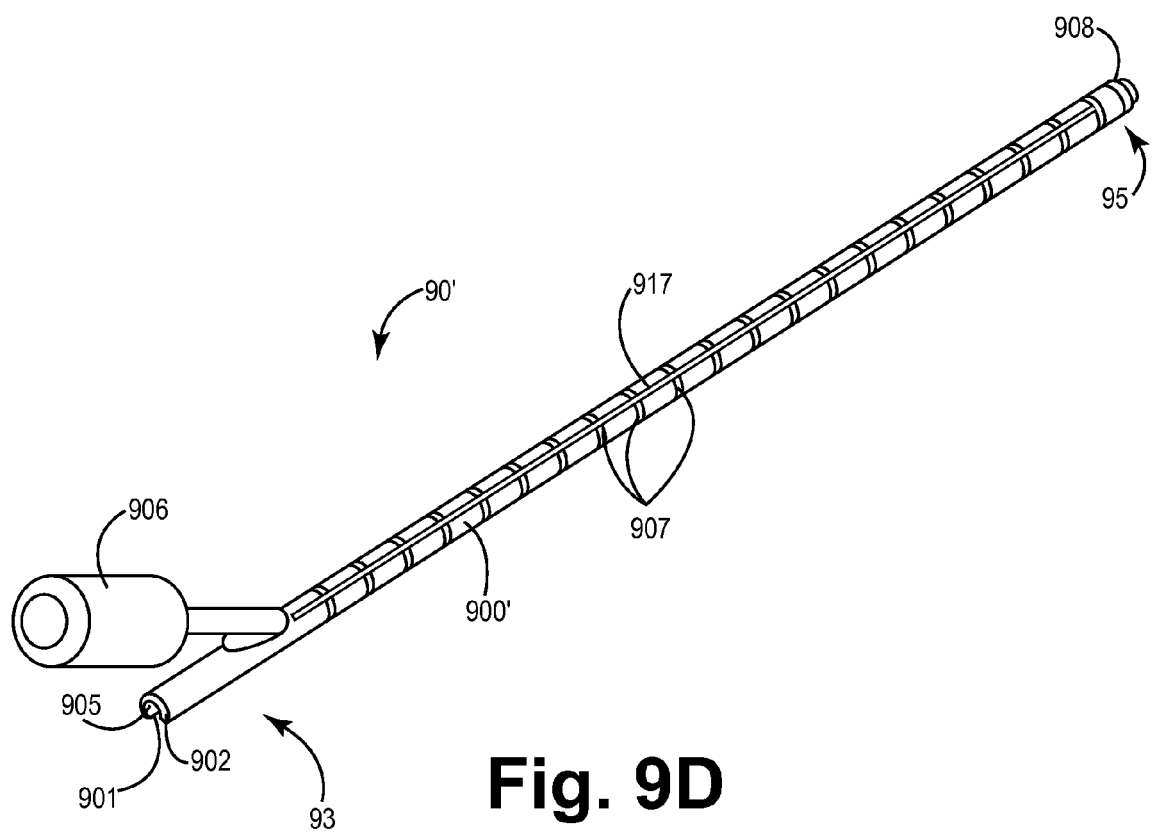

FIG. 9D is a perspective view of another access sheath, according to further embodiments of the present invention.

Figure 10:
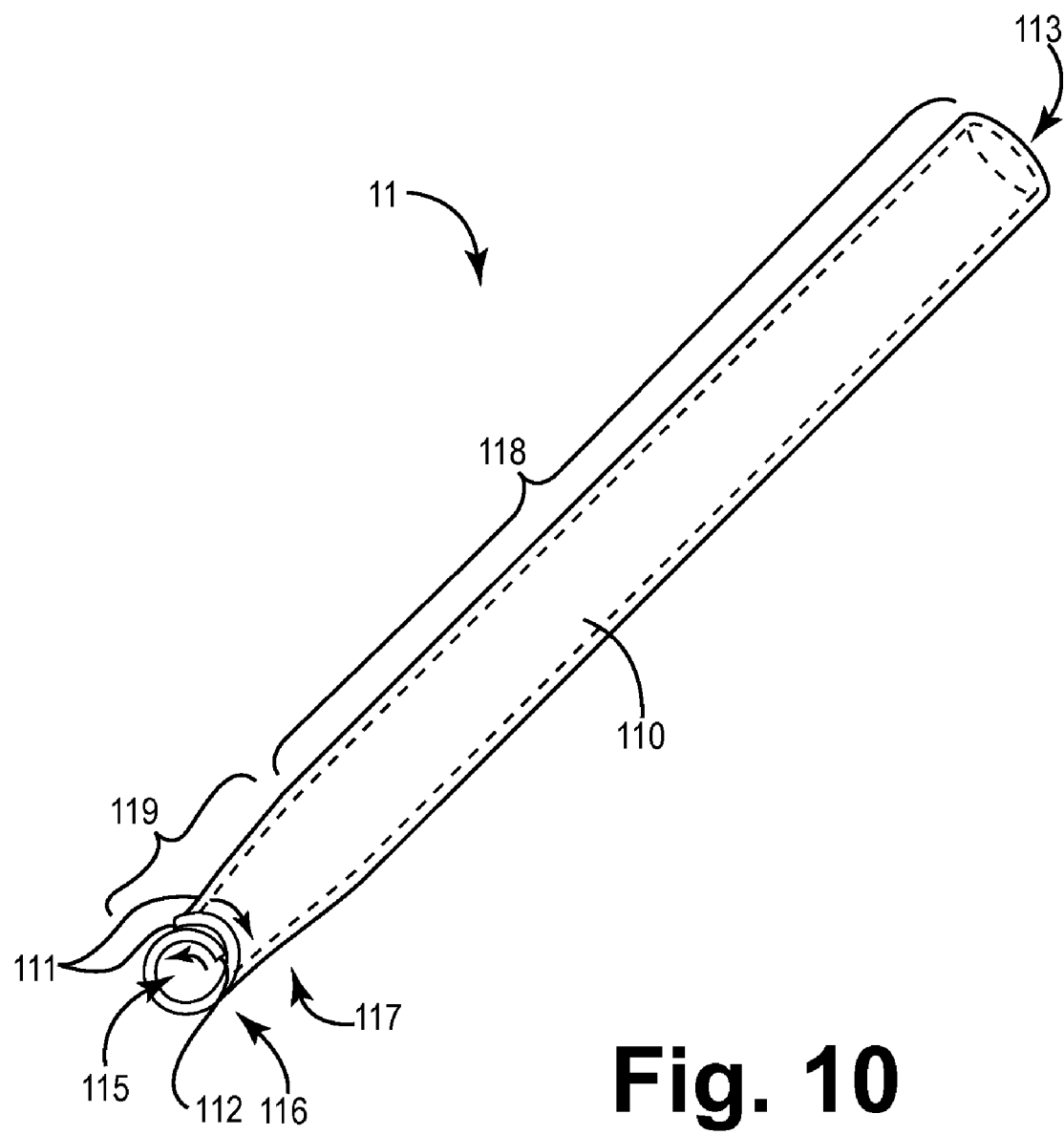

FIG. 10 is a perspective view of another type of access sheath, according to some embodiments of the present invention.

FIG. 11A is an exploded perspective view of an access sheath, according to alternate embodiments of the present invention.

FIG. 11B is a perspective view of the device body being inserted into the sheath of FIG. 11A.

Figure 11E:
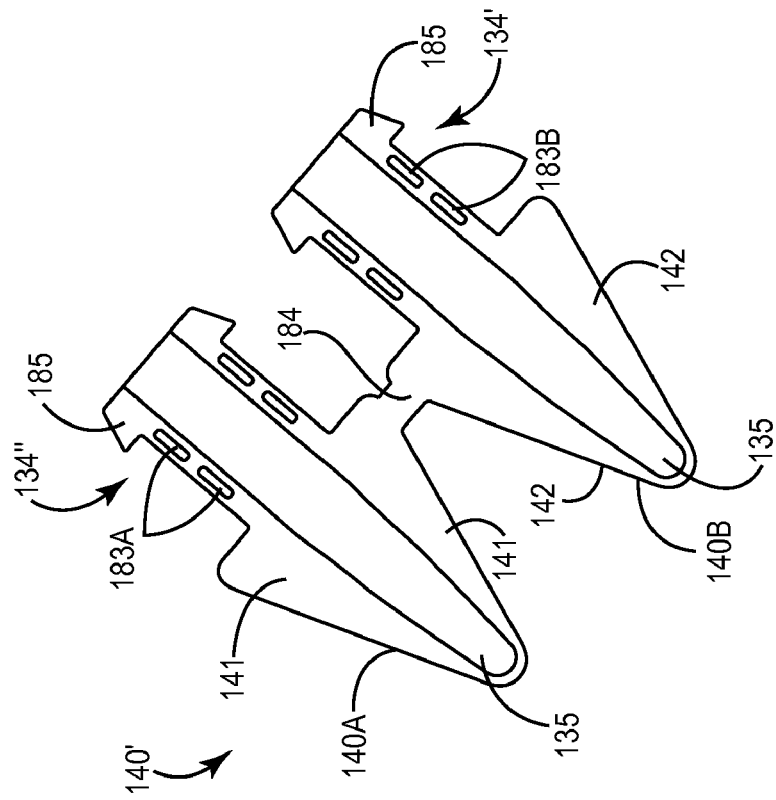
Figure 11C:
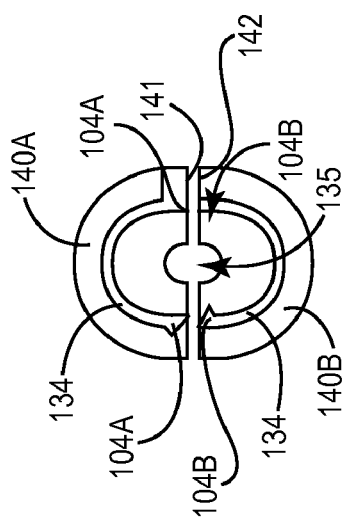

FIG. 11C is a section view through section line X-X of FIG. 11A.

Figure 11D:
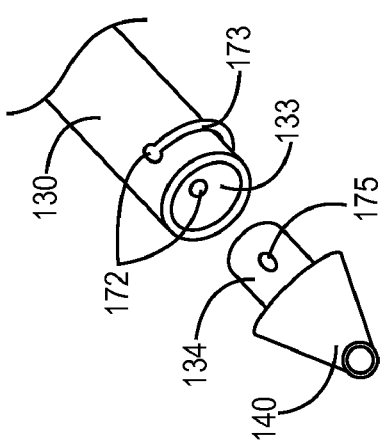

FIG. 11D is a perspective detail view of a portion of the sheath of FIG. 11A, according an alternate embodiment.

FIG. 11E is a perspective detail view of part of a sheath, according to yet another embodiment of the present invention.

Figure 12:
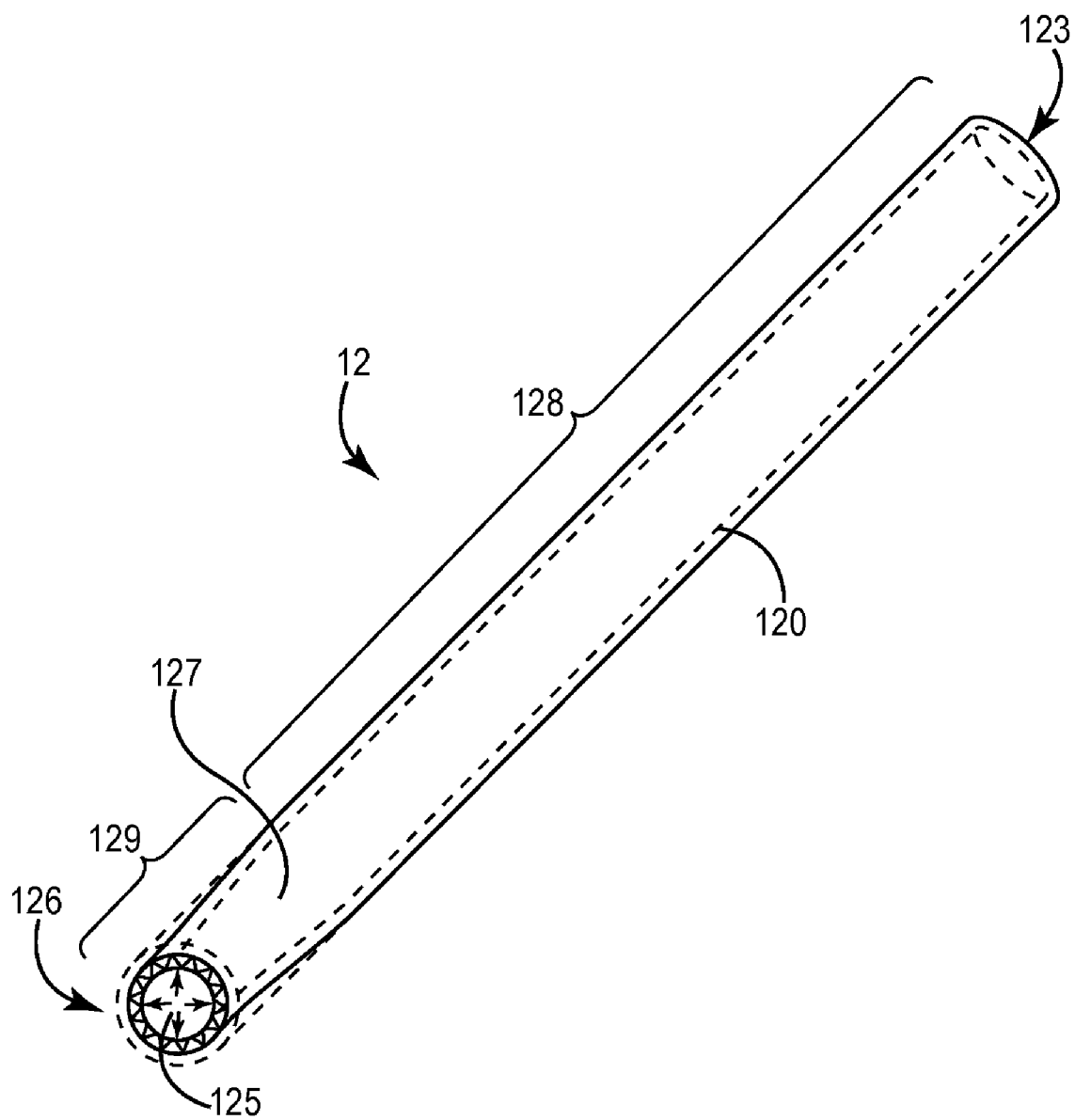

FIG. 12 is a perspective view of another access sheath, according to yet further embodiments of the present invention.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
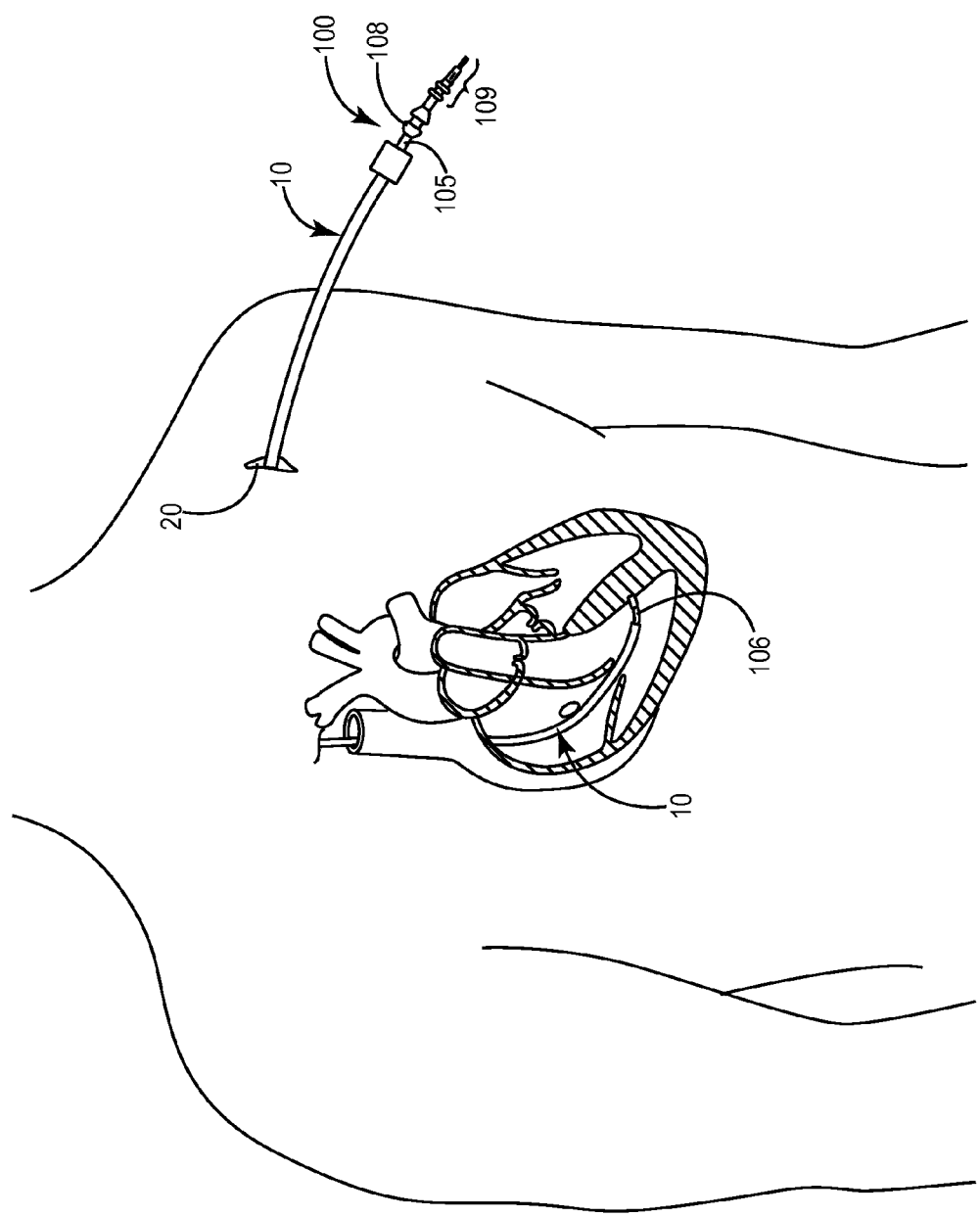
FIG. 1 is a schematic depiction showing an exemplary elongate device implanted in a heart of a patient via a delivery catheter.

FIG. 1 is a schematic depiction showing an elongate device 100, for example, a medical electrical lead, implanted in a heart of a patient via a delivery catheter 10. FIG. 1 illustrates catheter 10 extending transcutaneously and transvenously into the patient's heart via a venous access site 20; a body of device 100 is shown extending within catheter 10 such that a device body distal portion 106 extends distally from catheter 10, for fixation along a septum in a right ventricle (RV) of the heart, and a device body proximal portion 105 extends proximally from catheter 10. According to FIG. 1, device 100 further includes a connector 109, for example, an industry standard IS-1 connector, terminating body proximal portion 105. Once device 100 is implanted, catheter 10 may be removed from the patient by splitting a wall of the catheter lengthwise and peeling catheter 10 away from around the device body as catheter 10 is pulled out from the venous system; such a method for removing catheter may be necessary due to a limited length of device 100 and/or due to a maximum outer diameter of connector 109 being larger than an inner diameter of catheter 10. FIG. 1 further illustrates an optional anchoring sleeve 108 mounted around body proximal portion 105; an outer diameter of sleeve 108 may, like that of connector 109, be larger than an inner diameter of catheter 10.

Figure 2:
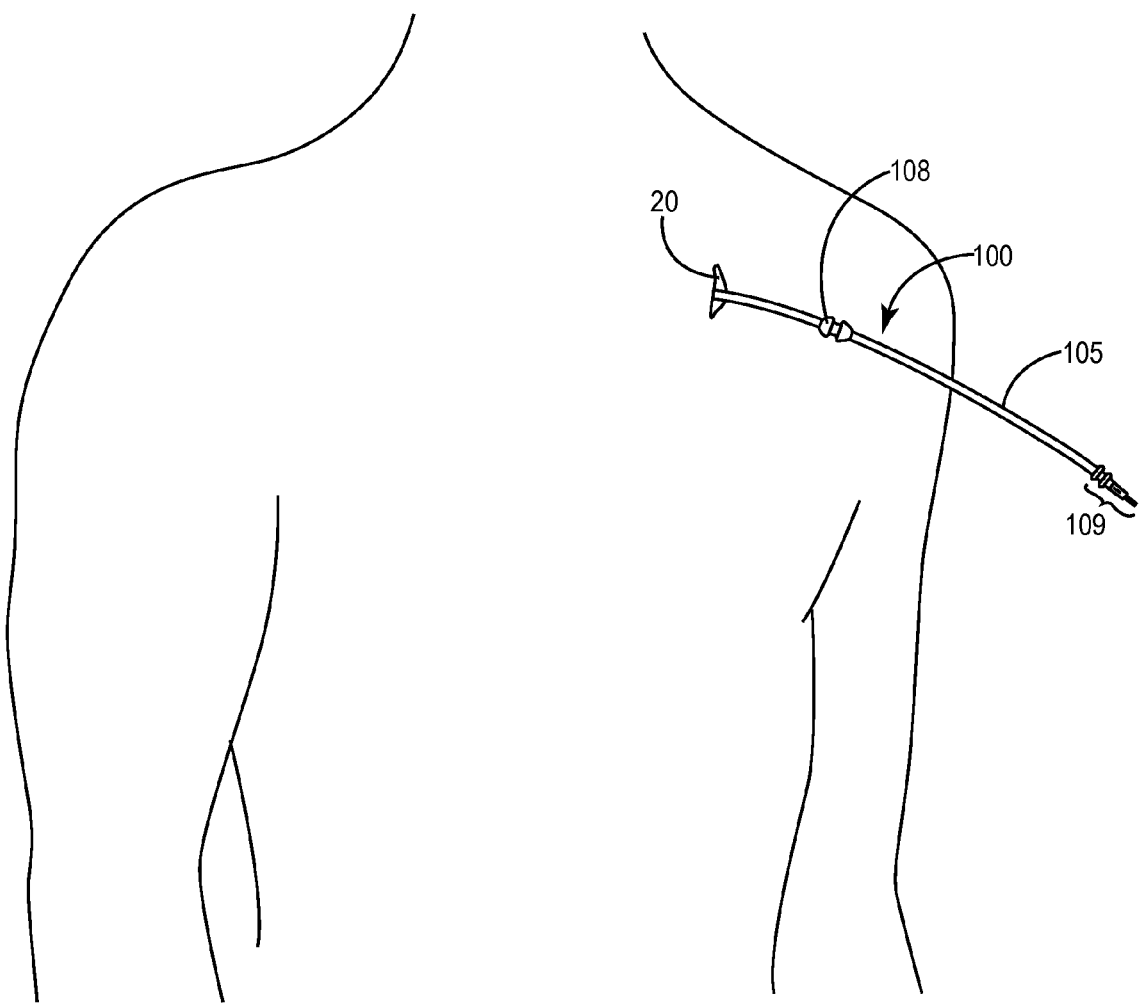
FIG. 2 is a schematic depiction showing a proximal portion of a body of the implanted device extending from a venous access site.

FIG. 2 is a schematic depiction showing body proximal portion 105 extending from venous access site 20 after catheter 10 has been removed. Those skilled in the art understand that connector 109 is useful for coupling device 100 to another device, either external to the patient, or subcutaneously implanted within the patient, which may facilitate therapy delivery and/or diagnostic measurements, for example, a pacemaker type device. However, before coupling connector 109 to the other device, an implanting physician typically verifies an implant location for device 100, for example, fixation along the RV septum as illustrated in FIG. 1. If the physician desires to change the implant location, or device 100 has become dislodged from the originally intended location during the process of removing catheter 10, the physician will need to re-gain venous access in order to reposition device 100. If the device body does not include an elongate lumen providing venous access for a stylet or guidewire, the physician will need to re-gain access alongside device body proximal portion 105, or, preferably, around device body proximal portion 105, so that another delivery catheter may be inserted into the venous system. According to certain embodiments of the present invention, access may be gained around device body proximal portion 105 without concern for the potentially larger diameters of connector 109 and optional anchoring sleeve 108.

FIG. 3A is a plan view of an access sheath 30, according to some embodiments of the present invention. FIG. 3A illustrates sheath 30 including a sheath wall 300 surrounding an elongate lumen 305 and including a first edge 301 and a second edge 302. According to the illustrated embodiment, first and second edges 301, 302 extend from a proximal end 33 of lumen 305 to a distal end 35 of lumen 305, and sheath wall 300 allows at least one of edges 301, 302 to spread apart from the other of edges 301, 302, for example, via arrows A, so that a device body may be inserted into lumen 305, for example, as illustrated in FIG. 3B. FIG. 3B is a perspective view of device body proximal portion 105 being inserted into lumen 305 of sheath 30. With reference to FIG. 3B, it may be appreciated that body 105 may be inserted into sheath lumen 305 without concern for a fit of either connector 109 or anchoring sleeve 108 (FIGS. 1-2) within lumen 305.

FIG. 3A further illustrates sheath 30 including a handle 306, coupled to an external surface of wall 300 at proximal end 33, and an enlarged gap 303 between first and second edges 301, 302, which may facilitate entry of a device body into lumen 305, between first and second edges 301, 302 at proximal end 33. It should be noted that although FIG. 3A shows a smaller gap between edges 301, 302, distal to gap 303, such a gap is not necessary, and according to an alternate embodiment, edges 301, 302 contact one another, when wall 300 is not deformed. Dashed lines in FIG. 3A illustrate an alternate embodiment of edges 301, 302 including interlocking features, for example, according to a zipper-like configuration; these features may extend along greater length of lumen 305 than is shown. Sheath wall 300 may be formed of one or more biocompatible materials having sufficient resiliency, for example, a polymer such as high density polyethylene or polytetrafluoroethylene (PTFE), or from a composite of a polymer and a metal reinforcing material, for example, a stainless steel braid embedded in a nylon material such as a poly ether block amide, for example, known as Pebax®.

FIG. 3C is a schematic depiction showing sheath 30 inserted into the venous system, around device body proximal portion 105, at access site 20. With reference back to FIGS. 3A-B, it may be appreciated that once body proximal portion 105 has been inserted into lumen 305, via separation, or spreading of edges 301, 302, sheath 30 may be advanced over body 105 and into the venous system, at access site 20, being facilitated by a tapering 308 of the external surface of sheath wall 300 at distal end 35. In order to minimize friction between an internal surface of wall 300 and body 105, the internal surface may include a lubricious coating extending thereover, for example, of the hydrophilic type known to those skilled in the art. With further reference to FIG. 3A, a radiopaque marker band 310, for example, a gold or platinum band, or a polymer band loaded with a filler such as barium sulfate, is shown coupled to wall 300 in proximity to distal end 35 for fluoroscopic visualization of sheath 30 within the venous system. According to some embodiments, marker band 310 may be echogenic for ultrasound 'visibility', for example formed from a tungsten carbide-filled polymer. An interlocking of edges 301, 302, for example, the features shown by dashed lines in FIG. 3A, may be desirable in order to lend compressive strength to sheath wall 300 as distal end 35 is inserted into the venous system at access site 20 and/or to limit blood loss out from access site, and/or air entry into access site, once sheath 30 is inserted into the venous system; additional sheath embodiments including alternate features taking on one or both of these functions will be described below in conjunction with FIGS. 4A-B.

A diameter of sheath lumen 305 may be large enough to accommodate a guidewire alongside device body 105, and FIG. 3C further illustrates a guidewire 39 positioned for insertion, per arrow C, into sheath 30, alongside device body 105. According to the illustrated embodiment, once guidewire 39 is inserted into the venous system, a new delivery catheter can be advanced over guidewire 39 and steered into the RV for the repositioning of device 100 therethrough. Sheath 30 and/or device 100 may be removed from the venous system prior to advancing the new delivery catheter over guidewire 39.

FIGS. 4A-B are perspective views of alternate embodiments of access sheaths, which include reversible closures. FIG. 4A illustrates a sheath 30' including a peel-away member 40, which extends across from a first edge 301 of a sheath wall 300 to a second edge 302 of wall 300, and forms the reversible closure for sheath 30'. Member 40 may include a tacky surface for reversible attachment to the exterior surface of sheath wall 300. FIG. 4B illustrates a sheath 48 including a sheath wall 410 surrounding an elongate lumen 415; wall 410 includes a first edge 411 and a second edge 412, each extending from a proximal end 43 to a distal end 45, and a tapered distal tip 417. According to the illustrated embodiment, portions of edges 411, 412 that extend proximal to tip 417 are spaced apart from one another by a greater distance than portions of edges 411, 412, which extend along tip 417 to distal end 45 and may touch one another. FIG. 4B further illustrates another wall 420 forming the reversible closure for sheath 48; wall 420 surrounds lumen 415, being slideably engaged within sheath wall 410, and includes a first edge 421 and a second edge 422.

According to the illustrated embodiment, when edges 421, 422 of wall 420 are aligned, via rotation, per arrow D, with edges 411, 412 of sheath wall 410, a device body may be inserted into lumen 415 in a manner similar to that illustrated in FIG. 3B. Once the body is inserted into lumen 415, wall 420 may be rotated, per arrow D, so that edges 421, 422 are offset from edges 410, 411, or no longer in alignment with edges 410, 411, in order to close the gap between edges 410, 411. Although wall 420 is shown extended proximally from proximal end 43 of sheath wall 410, thereby extending lumen 415 proximally from wall 410, wall 420 need not be extendable and retractable with respect to sheath wall 410, per arrow B, as illustrated, but may be held in a fixed longitudinal position with respect to sheath wall 410 while still being rotatable within wall 410. Sheath walls 410, 420, like sheath wall 300, may be formed of one or more biocompatible materials having sufficient resiliency, for example, a polymer such as low or high density polyethylene, or PTFE, or Pebax®.

FIG. 5A is a plan view of an access sheath 50, according to another embodiment of the present invention; and FIG. 5B is a longitudinal section view through the sheath of FIG. 5A in which device body 105 is inserted. FIGS. 5A-B illustrate sheath 50 including a sheath wall 500, which surrounds a first lumen 503 and a second lumen 505 and extends from a proximal end 53 of lumen 503 to a distal end 55 of lumen 505 where an exterior surface of wall 500 terminates in a tapered tip 508 to facilitate insertion into the venous system; wall 500 is shown including first and second edges 501 and 502 each extending from a proximal end 54 of second lumen 505 to distal end 55. FIGS. 5A-B further illustrate an enlarged gap 57, between first and second edges 501, 502, to facilitate insertion of device body 105 into lumen 505 between first and second edges 501, 502 at proximal end 54, for example, as previously described for gap 303 of sheath 30 (FIGS. 3A-B). According to the illustrated embodiment, once body 105 has been inserted into lumen 505 and sheath 50 has been advanced into the venous system, guidewire 39 may be inserted into proximal end 53 and advanced into the venous system through lumens 503 and 505. Sheath wall 500, like sheath wall 300, may be formed of one or more biocompatible materials having sufficient resiliency, for example, a polymer such as low or high density polyethylene, or PTFE, or Pebax®.

FIG. 6A is a perspective view of an insertion tool 60, according to some embodiments of the present invention, which may be used to facilitate insertion of a device body into an access sheath, for example, device body proximal portion 105 into sheath 30. FIG. 6B is a perspective view of tool 60 mounted on body 105 to draw body 105 into lumen 305 sheath of sheath 30, according to some embodiments of the present invention. FIG. 6A illustrates tool 60 including an elongate groove 62 and a leading edge 64, formed by a wall 600, and a handle portion 66 extending laterally with respect to groove 62. According to preferred embodiments of the present invention, tool 60 is formed from a relatively hard or rigid plastic having sufficient resiliency grip around body 105, for example, polyethylene, polypropylene, nylon, acrylonitrile-butadiene-styrene (ABS). Once tool 60 has been mounted on body 105 so that groove 62 grasps about a circumference of body 105, one of at least two methods may be employed to insert body 105 into lumen 305.

With reference to FIG. 6B, according to a first method, tool leading edge 64 is disposed in proximity to proximal end 33 of sheath lumen 305 and positioned to spread sheath wall edges 301, 302 apart by advancing tool over body 105, per arrow E; advancing tool 60 over body 105 draws a segment 162 of body 105, which is distal to tool 60, into lumen 305, per arrow F, between edges 301, 302, which are spread apart by the advance of tool leading edge 64. FIG. 6B further illustrates a second method wherein tool 60 grasps device body 105 to pull, per arrow G, a segment 161 of device body 105, which is proximal to tool 60, into lumen 305 behind the advance of the tool leading edge 64 which spreads edges 301, 302.

FIG. 7A is a perspective view of another insertion tool 70, according to alternate embodiments of the present invention; and FIG. 7B is a plan view of tool 70 mounted on device body proximal portion 105 and engaged with access sheath 30. FIG. 7A illustrates tool 70 including an elongate groove 72, for grasping about a circumference of a lead body, for example, body 105, a leading edge 74, being approximately aligned with groove 72, and a handle portion 76, extending laterally with respect to groove 72 and having a relatively flat surface in which a recess 71, which is sized to accommodate the device body, is formed. Tool 70 may be formed from a relatively hard plastic, for example, any of the materials previously designated suitable for tool 60, preferably polypropylene. With reference to FIG. 7B, it may be appreciated that while tool groove 72 grasps about body 105, recess 71 facilitates holding of body segment 161, which is proximal to that portion of body 105 grasped in groove 62, against handle portion 76.

FIG. 7B further illustrates tool leading edge 74 inserted within distal end 35 of sheath lumen 305, and sheath wall 300 oriented such that inserted leading edge 74 is poised to spread edges 301, 302 of sheath wall 300 as sheath 30 is advanced, per arrow H, along tool 70 and device body 105. Dashed lines in FIG. 7B illustrate sheath 30 having been advanced past tool and into venous system, via access site 20, around body segment 162, which is distal to that portion of body 105 grasped in tool groove 72. Thus, according to the illustrated embodiment, an operator may hold tool 70 and device body 105 steady, or in a fixed location, while sheath 30 is advanced, over body 105, into the venous system.

FIG. 8A is a perspective view of yet another insertion tool 80, according to additional embodiments of the present invention; and FIG. 8B is a plan view of tool 80 mounted on device body proximal portion 105, and access sheath 30 mounted on tool 80. FIG. 8A illustrates tool 80 including an elongate groove 82, which is formed by a wall 820, and a protrusion 840 extending laterally with respect to groove 82 and being terminated by a leading edge 84; protrusion 840 is shown including an optional lumen 804, for example, for passage of a guidewire, which will be described in greater detail below. FIG. 8A further illustrates another optional lumen 802 extending within wall 820 alongside and approximately parallel to groove 82; optional lumen 802 will also be described in greater detail below. Tool 80 may be formed from a relatively hard plastic, for example, any of the materials previously designated suitable for tool 60, preferably polypropylene. With reference to FIG. 8B, it may be appreciated that tool 80 is mounted on device body proximal portion 105 such that protrusion 840, shown with dashed lines within sheath 30, is directed proximally toward connector 109 that terminates body proximal portion 105. FIG. 8B further illustrates sheath 30 having been passed over leading edge 84 of protrusion 840 such that edges 301, 302 of sheath wall 300 are spread; it may be appreciated that an orientation of protrusion 840 assists in advancing sheath 30, per arrow J, along tool 80, around tool wall 820 and device body 105, and subsequently into access site 20, for example, as illustrated in FIG. 8C. According to the illustrated embodiment, an operator may grasp a proximal portion 825 of tool 80 and body 105, to hold both steady, while advancing sheath 30, per arrow J.

FIG. 8C further illustrates guidewire 39 having been passed through lumen 804 of protrusion 840 and alongside body 105 within sheath lumen 305. It should be noted that dashed lines in FIG. 8C indicate portions of body 105, tool 80 and guidewire 39 which would be hidden within tool and sheath walls. According to some embodiments, lumen 804 extends from leading edge 84, through protrusion 840 and wall 820, to groove 82, and tool 80 does not include lumen 802 shown in FIG. 8A; while, according to some other embodiments lumen 804 joins with lumen 802, which extends alongside groove 82. Although an opening of optional lumen 802 is shown at a first end 83 of tool 80 in FIG. 8A, so that it can be inferred that lumen 802 extends along an entire length of groove 82, it should be noted that lumen 802 need only extend from a junction with lumen 804 to a second end 85 of tool 80. According to some alternate embodiments, tool 80 does not include lumen 804 and only includes lumen 802 extending along an entire length of groove 82, which may be used for passage of a guidewire; the guidewire may be passed through lumen 802 and into sheath once sheath is positioned about body 105 as illustrated in FIG. 8C. Of course, a guidewire may be passed through either of lumens 804, 802, prior to inserting body 105 into sheath 30, and sheath 30 may be advanced around tool 80, body 105 and the guidewire. Alternately, device body 105 may be removed from groove 82 after sheath 30 is advanced over tool 80 and body 105 into the venous system, and then a guidewire inserted into the venous system via groove 82; thus, according to some other alternate embodiments, tool 80 includes neither of lumens 804 and 802.

FIG. 9A is a perspective view of an access sheath 90, according to additional embodiments of the present invention. FIG. 9A illustrates sheath 90 including a sheath wall 900 surrounding a lumen 905; sheath wall 900 includes an exterior surface, which tapers down to a distal tip 908, and first and second edges 901, 902, which are spaced apart from one another and extend along an entire length of lumen 905 from a proximal end 93 to a distal end 95 thereof. FIG. 9A further illustrates sheath 90 including a protrusion 906, which extends laterally with respect to lumen 905; a lumen 965 extends within protrusion 906 and either passes into lumen 905 through wall 900, for example, as illustrated in FIG. 9B, or passes into wall 900 and extends within wall 900 alongside lumen 905, for example, as illustrated in FIG. 9C. Preferably, wall 900 tapers from both the external surface and an internal surface at distal tip 908 and extends just beyond a distal opening of lumen 965 for the embodiment of FIG. 9C. Lumen 965, in any of the illustrated embodiments, may be used for passage of a guidewire, for example, into the venous system, once sheath 900 has gained access around device body 105.

According to the illustrated embodiment, a device body, for example device body proximal portion 105, is inserted into lumen 905 between edges 901, 902; a gap between edges 901, 902 may be sufficient such that an insertion tool, for example, any of those previously described, is not necessary to facilitate insertion of the device body into lumen 905 between edges 901, 902. According to an exemplary embodiment, for a device body having a diameter between approximately 0.040 inch and approximately 0.091 inch, edges 901, 902 are spaced apart from one another a distance between approximately 0.02 inch and approximately 0.05 inch, and an inner diameter of lumen 905 is between approximately 0.03 inch and approximately 0.05 inch. Those skilled in the art will understand that these exemplary dimensions may be 'tweaked' in order that sheath 900 may hold any diameter of device body, for example, ranging from approximately 0.013 inch up to approximately 0.130 inch. According to some embodiments of the present invention, lumen 905 of sheath 90 may have a variable inner diameter, for example, being larger in proximity to proximal end 93 and being smaller in proximity to distal end 95; such an inner diameter may change in a 'step' fashion at a discrete point between proximal end 93 and distal end 95, or taper down in size over a length between proximal end 93 and distal end 95. Sheath 90 may be formed from low or high density polyethylene, polypropylene, PTFE, nylon, acrylonitrile-butadiene-styrene (ABS).

FIG. 9D is a perspective view of another access sheath 90', according to further embodiments of the present invention. FIG. 9D illustrates sheath 90' being similar to sheath 90 of FIG. 9A, but having a wall 900' including ribs 907, which are either embedded therein or extend about an external surface or an internal surface thereof; ribs 907 are shown spaced apart from one another along a length of wall 900' and joined together by a column 917. According to the illustrated embodiment, ribs 907 form a reinforcing member that enhances radial stiffness of wall 900' without impairing a longitudinal flexibility of wall 900'. It should be noted that ribs 907 may be included along an entire length of wall 900' or just along a portion of the length. According to the preferred embodiments, wall 900' is formed from a relatively flexible polymer material, for example, nylon, polypropylene, ABS, etc., and spaced-apart ribs 907 are formed of a more rigid metal or polymer material, for example, stainless steel or poly ether ketone (PEEK), having spring-like properties to enhance a radial gripping force of wall 900' without impairing a 'trackability' or 'slideability' of sheath 90' over a device body. Ribs 907 and column 917 may be formed integrally, for example, laser cut from stainless steel, nitinol or a rigid polymer tubing stock having a wall thickness of approximately 0.010 inch. Ribs 907 and column 917 may subsequently be mounted on wall 900', or wall 900' molded around ribs 907 and column 917, for example, via insert molding or via a coating process. According to some alternate embodiments, wall 900', ribs 907 and column 917 are integrally formed from a single polymer material, for example, via a molding process, wherein wall 900' between ribs 907 is thinner for increased flexibility.

FIG. 10 is a perspective view of another type of access sheath, according to some embodiments the present invention. FIG. 10 illustrates a sheath 11 including a sheath wall 110 surrounding an elongate lumen 115, which extends from a proximal end 113 to a distal end 116, and a first edge 111 and a second edge 112, which extend along a distal portion 119 of lumen; first edge 111 is shown overlapping second edge 112 to create a tapered tip 117 thereby reducing a diameter of lumen distal portion 119 toward distal end 116. FIG. 10 further illustrates a lumen proximal portion 118 having a diameter which is larger than that of lumen distal portion 119 at distal end 116. According to the illustrated embodiment, edges 111, 112 of wall 110 may slide with respect to one another to expand the diameter of lumen distal portion 119 to a diameter approximately equal to that of lumen proximal portion 118 so that a device body proximal portion having an enlarged proximal end, for example body 105 terminated by connector 109 shown in preceding figures, may be inserted into lumen 115 at distal end 116. According to an exemplary embodiment of the present invention, the expanded diameter of lumen distal portion 119 and the diameter of lumen proximal portion 118 are each large enough to slide over an industry standard IS-1 connector. After the enlarged proximal end of a device body has passed through the expanded diameter, edges 111, 112 may slide back into a position similar to that illustrated in FIG. 10, preferably to a diameter only slightly greater than a diameter of the device body in order to fit snugly thereabout and thereby increase the ease of advancing tip 117 over the body and into the venous system.

FIG. 11A is an exploded perspective view of an access sheath 13, according to alternate embodiments of the present invention. FIG. 11A illustrates sheath 13 including a wall proximal part 130 surrounding a proximal lumen 133, and a wall distal part 140 surrounding a distal lumen 135 and forming a tapered tip 114; a diameter of proximal lumen 133 is greater than that of distal lumen 135, and distal part 140 includes first and second edges 141, 142 which split distal part 140 into a first portion 140A and a second portion 140B so that wall distal part 140 is reversibly expandable to allow for expansion of distal lumen 135. FIG. 11A further illustrates wall distal part 140 including an engagement portion 134 for reversibly engaging tip 114 to wall proximal part 130; engagement portion 134 is shown including male threads 107 as a means for reversible engagement with female threads 103 disposed on an inner surface of wall proximal part 130.

According to the illustrated embodiment, in order to insert a device body, for example device body proximal portion 105, into lumens 133 and 135 of sheath 13, distal tip 114 is first disengaged from wall proximal part 130 by unscrewing wall distal part 140, and then an enlarged proximal end of the device body, for example connector 109, is inserted through lumen 133 of proximal part 130, which has a sufficiently sized lumen diameter. In FIG. 11B, body 105 is shown inserted into wall proximal part 130. The device body is then inserted into distal lumen 135 of sheath 13 by first spreading apart first and second edges 141, 142, per arrows M (FIG. 11A), and then bringing portions 140A, 140B back together around the body so that edges 141, 142 mate, for example, as shown in FIG. 11B, and then engaging tip 114 with wall proximal part 130 by screwing distal part 140 thereto. Any suitable alternate means known to those skilled in the art, for reversibly engaging wall proximal part 130 with wall distal part 140 may be employed, and examples of these include, without limitation, a press fit, interlocking detents, opposing magnets, and a bayonet-type interlock. For example, a magnetic ring may be substituted for female threads 103, within wall proximal part 130, and an opposing magnetic ring may be substituted for male threads 107, about outside of engagement potion 134.

According to some embodiments of sheath 13, edges 141, 142 include means for reversible engagement, and FIG. 11C is a section view through section line X-X of FIG. 11A illustrating an example of such means. In FIG. 11A, edge 141 includes external projections 104A for interlocking with internal projections 104B of edge 142; applying an external compressive force to first portion 140A may serve to release the interlocking of projections 104A, 104B so that edges 141, 142, and, thus portions 140A and 140B, can be separated from one another.

FIG. 11D is a perspective detail view of an alternate means for reversible engagement of wall distal part 140 with wall proximal part 130. FIG. 11D illustrates proximal part 130 including a spring clip 173, which includes ends extending through opposing holes 172 of wall 130 to couple clip 173 to wall 130; engagement portion 134 of distal part 140 includes opposing holes 175 extending therethrough to receive ends of spring clip 173 when portion 134 is inserted into proximal lumen 133. Although not shown, according to preferred embodiments, an external surface of wall proximal part 130 includes a recess to accommodate clip 173 so that clip 173 is recessed with respect to, or flush with, an exterior surface of wall 130.

FIG. 11E is a perspective detail view of a wall distal part 140' which may be reversibly engaged by wall proximal part 130 sheath 13, according to yet another embodiment of the present invention. FIG. 11E illustrates wall distal part 140' wherein edges 141 and 142 of first and second portions 140A and 140B are opened away from one another, and portion 140A is joined to portion 140B by a hinge 184. With reference to FIG. 11E, in conjunction with the method described above in conjunction with FIGS. 11A-B, it may be appreciated how hinge 184 can facilitate the handling of distal part 140' for insertion of the device body into distal lumen 135.

FIG. 11E further illustrates portions of first and second edges 141 and 142, which extend along an engagement portion 134' of distal part 140', including interlocking features 183A and 183B, respectively. According to the illustrated embodiment, features 183A are recesses into which features 183B fit for reversible engagement of edge 141 against edge 142. Alternately, features 183A and 183B may be opposing magnets. Finally, FIG. 11E illustrates engagement portion 134' including a male detent feature 185 to mate with a female detent feature (not shown) in lieu of thread 103 along an inner surface of wall proximal part 130, as an alternate embodiment of means for reversibly engaging proximal and distal parts 130, 140'.

Components of the illustrated embodiments of sheath 13 may be formed from stainless steel, and/or from one or more relatively rigid, yet malleable, materials, for example, nitinol, nylon, Pebax®, PTFE or polypropylene.

FIG. 12 is a perspective view of another access sheath 12, according to yet further embodiments of the present invention. FIG. 12 illustrates sheath 12 including a sheath wall 120 surrounding an elongate lumen 125, which extends from a proximal end 123 to a distal end 126; sheath wall 120 is terminated by a tapered tip 127 thereby reducing a diameter of a lumen distal portion 129 toward distal end 126. FIG. 12 further illustrates a lumen proximal portion 128 having a diameter which is larger than that of lumen distal portion 129 at distal end 126. According to the illustrated embodiment, tapered tip 127 is reversibly expandable such that the reduced diameter of lumen distal portion 129 may be enlarged to approximate that of lumen proximal portion 128, so that a device body proximal portion having an enlarged proximal end, for example body 105 terminated by connector 109, may be inserted into lumen 125 at distal end 126. The reversible expansion of lumen distal portion 129 may be facilitated by incorporation of pre-formed folds formed in a portion of wall 120 at distal tip 127, and/or by incorporation of an elastic material, such as silicone or latex, and/or by incorporation of an electro-active polymer, the expansion and contraction of which is in response to an applied voltage, and/or by incorporation of an inflatable bladder. According to an exemplary embodiment of the present invention, the expanded diameter of lumen distal portion 129 and the diameter of lumen proximal portion 128 are each large enough to slide over an industry standard IS-1 connector. After the enlarged proximal end of a device body has passed through the expanded diameter, lumen distal portion 129 may contract to a diameter only slightly greater than a diameter of the device body in order to fit snugly thereabout and thereby increase the ease of advancing tip 127 over the body and into the venous system.

In the foregoing detailed description, the invention has been described with reference to specific embodiments. However, it may be appreciated that various modifications and changes can be made without departing from the scope of the invention as set forth in the appended claims; for example, suitable materials and methods for forming embodiments of the present invention are by no means limited to the examples described herein. Furthermore, although embodiments of the present invention have been described in the context of gaining venous access, it should be understood that embodiments of the present invention may be employed for gaining access into other areas, outside the venous system, of a patient's body where an elongate medical device may have been implanted.

We claim:

1. A system for gaining access into a body of a patient around an implanted body of an elongate medical device, the system comprising:
   a sheath wall surrounding an elongate lumen, the wall including a first edge and a second edge, the elongate lumen including a proximal end and a distal end and having a diameter sized to fit about the device body, and the first and second edges extending from the proximal end to the distal end of the lumen; and
   an insertion tool for inserting the implanted device body into the elongate lumen, the insertion tool comprising a wall that forms an open elongate groove and a protrusion that extends out from the wall of the tool, on a side of the wall that is opposite the groove, the groove being sized to receive, along a length thereof, a portion of the implanted device body and to grasp about a circumference of the portion of the received body, the protrusion being terminated by an exposed leading edge, and the exposed leading edge being spaced apart from the wall of the tool and formed to spread the first and second edges of the sheath wall apart from one another;
   wherein the protrusion is oriented to direct advancement of the sheath wall, once the first and second edges of the sheath wall have been spread apart by the leading edge, onto the wall of the insertion tool and then around the implanted device body, when the portion of the body is received in the groove.

2. The system of claim 1, wherein the insertion tool further comprises a lumen extending within the wall of the tool, alongside the open groove, approximately parallel therewith, and along an entire length of the groove.

3. The system of claim 1, wherein the insertion tool further comprises a lumen extending from an opening at the exposed leading edge, through the protrusion, and into the open groove.

4. The system of claim 1, wherein the insertion tool further comprises a lumen extending from a first opening at the exposed leading edge, through the protrusion and within the wall of the tool, alongside the open groove, being approximately parallel to the groove, to a second opening at an end of the wall.

* * * * *